United States Patent [19]

Gripp et al.

[11] Patent Number: 4,954,337
[45] Date of Patent: Sep. 4, 1990

[54] NOVEL SHAVING COMPOSITION

[75] Inventors: Anna A. Gripp, Nutley; Gottfried Metzler, III, Brookside, both of N.J.

[73] Assignee: American Cyanamid Company, Stamford, Conn.

[21] Appl. No.: 198,909

[22] Filed: May 26, 1988

[51] Int. Cl.$^5$ ............................................. A61K 7/15
[52] U.S. Cl. ........................................ 424/73; 424/47; 514/772
[58] Field of Search ................ 424/73, 45, 47; 83/22; 30/41, 346, 346.5; 514/772

[56] References Cited

U.S. PATENT DOCUMENTS

| | | | |
|---|---|---|---|
| 2,292,417 | 8/1942 | Wetherbee | 424/73 |
| 3,715,942 | 2/1973 | Courtney | 424/73 X |
| 3,808,920 | 5/1974 | Fisher | 424/73 X |
| 3,949,067 | 4/1976 | Gibbs | 424/73 |
| 4,178,364 | 12/1979 | Rucker | 424/73 |

FOREIGN PATENT DOCUMENTS

| | | | |
|---|---|---|---|
| 668776 | 8/1963 | Canada | 424/73 |
| 57-194 | 12/1983 | Japan | 30/41 |
| 101310 | 5/1988 | Japan . | |
| 2013492 | 8/1979 | United Kingdom | 424/73 |

OTHER PUBLICATIONS

CTFA Dictionary, pp. 83–84, Reference to Dimethicone Copolyol, 3rd Edition, 1982.
Silwet Surface Active Copolymers, Technical Bulletin, Union Carbide Corp., pp. 1–4 (1980).

Primary Examiner—Merrell C. Cashion, Jr.
Assistant Examiner—Susan S. Rucker
Attorney, Agent, or Firm—Anthony M. Santini

[57] ABSTRACT

A composition for treating the blade of a razor by applying a non-foamable lubricant and solubilizer mixture via an aerosolization system directly to the razor blade immediately before shaving such that shaving can be performed in the absence of first applying any shaving preparation directly to the area to be shaved.

15 Claims, 2 Drawing Sheets

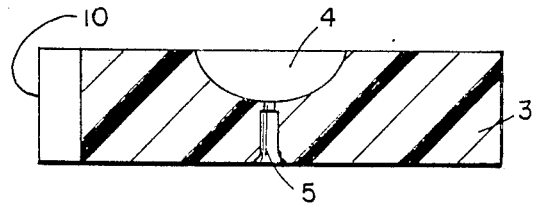
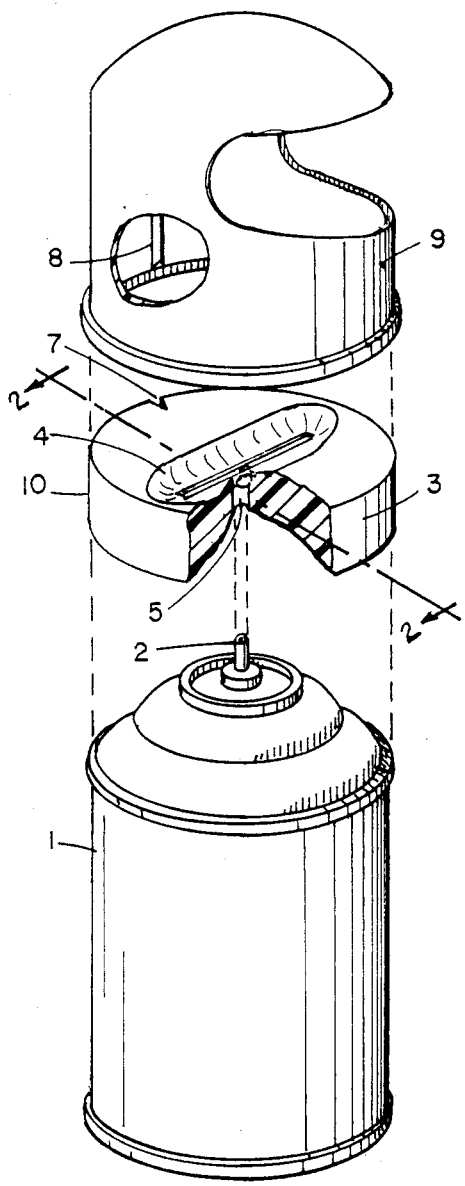
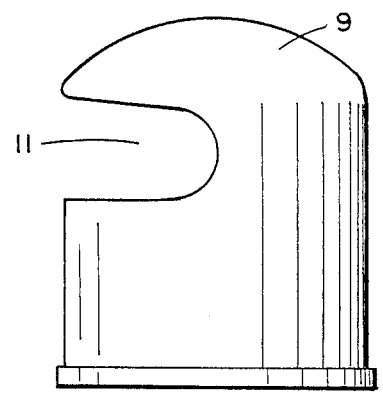
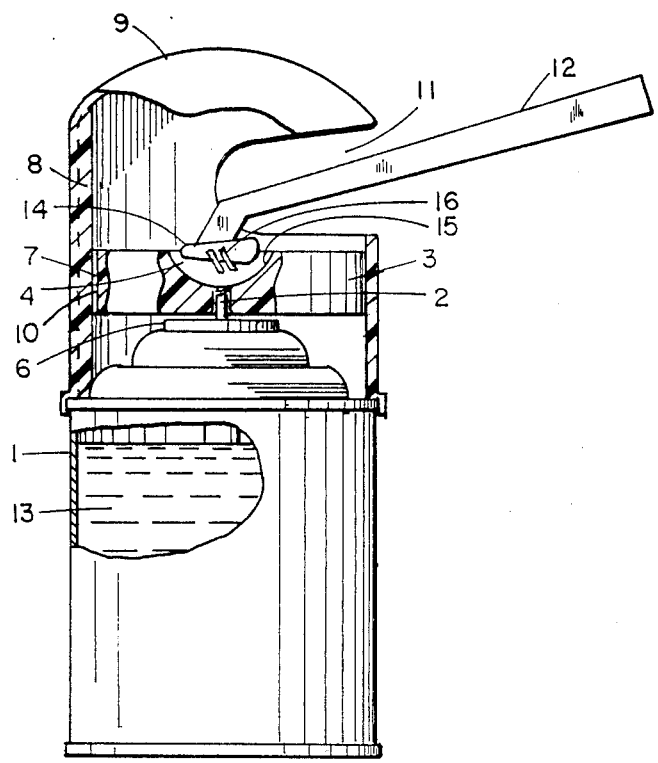

NOVEL SHAVING COMPOSITION

BACKGROUND OF THE INVENTION

From the Stone Age to the Space Age, mankind has been on an unending quest for the perfect shave. Between late prehistoric days to 3100 B.C., unwanted facial hair was removed by using anything from sharpened animals' teeth to volcanic glass. Over several centuries, sharpened metal was discovered to be the ultimate razor.

During the 4th Century B.C., Alexander the Great ordered his troops to be clean shaven so that enemies could not grab their beards in battle. During the 11th Century A.D., steel was introduced in razors.

In 1698, Czar Peter the Great of Russia levied a 'Beard Tax', forcing his reluctant male subjects to shave. During the 18th and 19th centuries, most American and European men depended on the barbershop for a shave.

In 1904, Massachusetts inventor King C. Gillette received a patent for the home safety razor. His company sold 90,000 razors and 12 million blades in its first year.

In 1931, the electric shaver was introduced and,, in 1959, coated, stainless-steel blades were invented. In 1971, the twin blade cartridge was marketed, followed in 1975 by the first disposable razor. In 1981, Gillette introduced the first swivelhead razor.

Today, American men spend over $1 Billion on razors and blades, and more than an additional $1.2 Billion on shaving creams, aftershaves and colognes.

Generally speaking, prior to the present invention, shaving was conventionally performed by applying lather directly to the area to be shaved. Shaving lathers were originally prepared by, for example, agitating a personal care soap with the use of a bristle brush to form a whipped composition. However, these lathering soaps were considered time-consuming and inconvenient.

Brushless creams were subsequently available for shaving purposes. The creams are spread upon the area to be shaved, in the state that they are purchased, and generally do not form a lather. However, they were less effective than the soap lathers because they did not permit as close or smooth a shave and, unless completely cleaned from the skin, left a greasy or sticky feeling.

In an attempt to improve methods of shaving, preparations packaged in aerosol containers, such as described in U.S. Pat. No. 2,655,840 to Spitzer et al., were introduced. A lather is produced as the composition released from the aerosol container, and then applied directly to the area to be shaved. Although still popular today, consumers' dissatisfaction with present aerosol lathers continues to exist, primarily due to the fact that most aerosol lathers provide improper wetting of the surface to be shaved, thereby resulting in an inferior shave.

U.S. Pat. No. 4,023,269 to Lopez discloses a handy device designed to improve skin preparation before shaving. A shaving cream is produced from an aerosol container, comprising the handle portion of the razor, and passes through the neck of the razor handle to be discharged through an integrally formed applicator brush. The brush is used to fully massage the shaving preparation onto the skin. A razor head, integrally connected to, but separate from, the brush, is then used to shave the treated skin surface. The razor blade forms a part of the shaving device merely as a convenience item. U.S. Pat. No. 3,417,468 to Miyauchi is analogous to the Lopez patent. Namely, a foamy skin preparation is absorbed onto a sponge applicator device for pretreatment of the skin before shaving. Once the preparation has been applied to the skin, a razor blade, formed integrally with, but separate from, the sponge applicator, is used to shave the pre-treated skin.

Other 'all-in-one' devices, such as disclosed in U.S. Pat. No. 3,726,009 to Hackmyer and U.S. Pat. No. 4,077,119 to Sellera, have been introduced wherein pressurized containers form the handle portion of the razor and dispense lathers up to and through the razor head to treat the skin immediately before shaving. However, these convenience items suffer from the disadvantages associated with messy foams and poor shave quality.

In a further attempt to improve shave quality, there was developed an aerosol system containing a post-foaming gel, as described in U.S. Pat. No. 3,541,581 to Monson. The aerosol container discharges a gel substantially free from foaming and, when spread over the skin, produces a self-generating foam having a substantially uniform foam profile.

In addition to the above items, there has been developed a system for use in shaving for treating the blade of a razor, as described in U.S. Pat. No. 4,642,893 to Borenstein, by applying a refrigerant directly thereto via an aerosol system to sharpen the blade of the razor. Unfortunately, this system makes shaving even more time-consuming, as it requires the cumbersome process of applying lather from one container directly to the skin, followed by the continuous cooling of the razor from another container during shaving.

Reservoir safety razors are also known. See, for example, U.S. Pat. No. 3,176,391 to Resnick et al. and U.S. Pat. No. 4,238,882 to Harrison. However, these also are directed to skin treatment such as, for instance, hydration. Treatment of the blade is not an objective.

The present invention eliminates the disadvantages associated with the aforementioned systems while providing a superior shave without the mess and bother associated with current shave creams and/or gels. This is achieved by providing a composition of a liquid lubricant and solubilizer mixture directly to the blade of the razor, via an aerosolization system, instead of onto the area to be shaved.

Although it has heretofore been known to apply a composition directly to the blade of a razor, such as described in U.S. Pat. No. 3,364,068 to Stern, the known systems are completely different in principle from the present invention.

U.S. Pat. No. 3,364,068 teaches the use of a pressurized container for applying biocidal gas to a razor head to clean the razor blades. U.S. Pat. No. 4,642,893 teaches the use of a pressurized container for applying a coolant to a razor head to freeze the razor blades. The present invention is directed to a composition applied to a razor blade via a pressurized container to lubricate the razor blade.

Basically, the present invention utilizes principles which are in contradiction to the prior art. This invention allows the user to apply a lubricant and solubilizer mixture directly to the blade of a razor instead of applying a shaving preparation directly to the area to be shaved. It has surprisingly been found that this composition provides significant improvements in razor glide, closeness and smoothness of shave, as well as better after-feel.

SUMMARY OF THE INVENTION

Briefly, what is provided is a novel shaving composition for use with a razor having at least one blade. In an embodiment of the invention, there is provided a lubricant, mixed with a solubilizer and, optionally, additional propellant(s), for application directly onto the blade of a razor. This is done immediately prior to contacting the skin with the razor, such that shaving can be performed in the absence of first applying any creams, foams or gels directly to the area to be shaved. The lubricant/solubilizer/propellant mixture is contained in, and applied via, a pressurized container. The container has an aerosol valve located at a discharge end thereof and a razor head contact element positioned around and atop the valve. A cap member, having an opening partially around a side thereof, is slidably mounted around the razor head contact element and removably fixed onto the container to provide safety-shielded product delivery. A razor head is then placed through said opening and momentarily pressed onto the contact element to actuate the valve and discharge the novel composition in the container directly and uniformly onto the blade of the razor head. The treated razor is then retracted from the apparatus and contacted onto the area to be shaved such that shaving can be performed without having to first apply any shaving preparation directly to the shaving area. The shaving area may or may not be hydrated, as desired. Thus, a composition is provided which is an attractive alternative to messy, conventional shave creams. The present system is neat, safe to use, convenient, and less time-consuming.

Accordingly, it is an object of the invention to provide a composition, for treating the blade of a razor head, which is convenient, inexpensive and easy to use.

It is also an object of the invention to provide a composition for treating the blade of a razor head to provide significant improvements in razor glide, closeness and smoothness of shave, as well as better after-feel.

It is a further object of the invention to provide a composition for treating the blade of a razor head to permit shaving in the absence of first applying any creams, foams or gels directly to the area to be shaved.

It is a still further object of the present invention to provide a composition, for treating the blade of a razor head, which can be used with most hand-held razor(s) having one or more blades.

It is an even further object of the present invention to provide a composition, for treating the blade of a razor head, which utilizes all of the above-mentioned principles.

Still other objects and features of the present invention will be more fully disclosed in the following detailed description, which is to be considered together with the accompanying drawings wherein like numbers refer to like parts and further wherein:

BRIEF DESCRIPTION OF THE DRAWINGS

FIG. 1 is a transverse view of a pressurized container apparatus for use with the composition of the invention;

FIG. 2 is a cross-sectional view of the razor head receiving element for use with the composition of the invention taken along line 2—2 of FIG. 1;

FIG. 3 is a side view of the removable cap for use with the composition of the invention;

FIG. 4 is a cross-sectional view of the apparatus of FIG. 1 containing the composition of the invention in use with a razor;

DETAILED DESCRIPTION OF THE INVENTION

Figure 5:
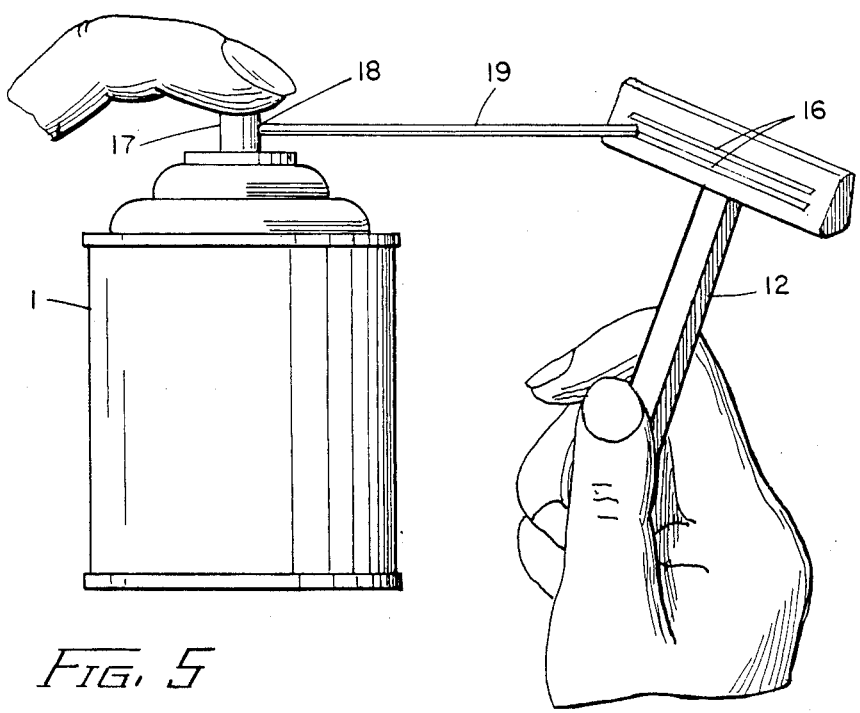
FIG. 5 is a transverse view illustrating an apparatus and operation of an alternative apparatus for use with the composition of the invention.

Referring to FIG. 1, there is shown container 1 for use with the composition of the invention having actuating valve means 2. Although any size container may be used, it is recommended that a squat container be employed so that the container does not tip when the valve means is actuated. Razor head contact element 3 is positioned atop and around valve means 2. Contact element 3 has a trough cut-out in the top and longitudinal center thereof with aperture 5 extending from the bottom center of contact element 3 up through trough 4. Contact element 3 further has notch 7 which is slidably engaged with ridge 8 along the inside surface of cap member 9.

As shown in FIGS. 1 and 4, when the apparatus is assembled, contact element 3 is radially disposed about and atop container 1 such that aperture 5 is concentric with valve means 2 and contact element 3 does not touch top area 6 of container 1. Cap member 9 is then positioned around peripheral wall portion 10 of contact element 3 to align ridge 8 with notch 7 and mount cap member 9 around contact element 3 and in removably fixed position with container 1. Ridge 8 prevents movement of contact element 3 in a horizontal or radial direction when positioned in notch 7.

As seen in FIG. 3, cap member 9 has opening 11, preferably partially around a side thereof, and is dimensioned to accommodate the passage of a razor head therethrough. In this manner, actuation of valve means 2 is possible without the removal of cap 9. The cap and razor head contact element may be fabricated from, but not limited to, metal or suitable synthetic resins such as thermoset and thermoplastic resins. By use of synthetic resins, complex formations may be readily molded therein by compression or injection molding techniques.

Referring to FIG. 4, there is shown an apparatus for use with the composition of the present invention in operation with razor 12. Container 1 contains a high-density mixture 13 of the lubricant and solubilizer and, optionally, additional propellant(s). The lubricant is preferably a non-foamable liquid lubricant. Non-foamable is defined as non-lathering compositions excluding, for example, soaps, creams and foams. An excellent lubricant of this nature is silicone glycol copolymer. Its CTFA name is dimethicone copolyol. This lubricant is water soluble, compatible in the present system and leaves a nice after-feel on the skin. Other lubricants which may be used include isopropyl myristate, mineral oil, cyclomethicone, dimethicone, trimethylsiloxysilicate, 2-octyl-1-dodecanol, (C12-15 alcohol benzoates) myristylproprionate, sorbitan monolaurate and sorbitan monolaurate 20, or any mixture thereof.

However, since the liquid lubricant exists in a suspended two-phase system, it requires the use of a solubilizer to form it into solution. It has been found that, if the liquid/solubilizer mixture maintains a pressure of at least about 5 psig at 70° F., the mixture also has suitable propellant properties. Dimethyl ether has been found to be an excellent solubilizer for this purpose.

It has also been found that, if the high-density mixture in the container maintains a vapor pressure of, preferably, at least about 50 psig at 70° F., the mixture also acts to cool the razor blade as it expands upon expulsion from the aerosol container. Thus, the cold metal blade will be sharper, as well as lubricated.

It has further been found that the economics of the present device can be improved by nonetheless optionally incorporating additional propellant(s) into the silicone glycol/dimethyl ether composition, partially replacing the more expensive dimethyl ether. The employed propellant can be any from the group consisting of propane, butane and isobutane. Examples of the foregoing are A-17, A-30, A-40, A-46 and A-70. Although numerous other propellants are commercially available, it has been found that the aforementioned propellants perform favorably and do not violate environmental concerns. As a further component, mixture 13 can also contain a fragrance, thereby eliminating the need for aftershave cologne.

It is preferred that the foregoing components be present in an amount within the following approximate ranges (expressed in percentages by weight):

| | |
|---|---|
| Lubricant | 4.0 to 20% |
| Solubilizer | 65 to 96% |
| Propellant | 0 to 14% |
| Fragrance | 0 to 1% |

Other ingredients which might also be added include surfactants (to assist in cleaning the razor), polymers (to protect the cutting edge), antimicrobials (to address acne) and other functional items.

Again, referring to FIG. 4, in its assembled form, razor 12 is placed through opening 11 of cap member 9 and razor head 14 is pressed onto downwardly tapering side walls 15 of trough area 4 thereby applying a momentary actuating downward pressure on valve means 2 to allow novel mixture 13 to escape from container 1 and through aperture 5 such that passage of the solution therethrough creates a uniform and even dispersion of the mixture onto razor blade 16.

Cap 9 is designed to avoid overspray and protect the user therefrom. Of course, cap member 9 can be of any design which allows for the insertion of a razor head through the side thereof and onto contact element 3.

After razor blade 16 is sufficiently treated, razor 12 can be withdrawn through opening 11 and directly contacted to the area to be shaved. Thus, according to the present invention, there is no need to first apply any shaving preparation to the shaving area. As is evident, a twin-blade razor is just as easily deployable as a single-blade razor.

FIG. 5 illustrates an alternative apparatus for use with the novel composition of the invention wherein hand-held container 1 has push-button-operated valve 17 and valve discharge port 18. Dispensing stem 19 is removably pressed-fitted into valve port 18 and provides a clear passageway for the lubricant/solubilizer contents of container 1 to exit from port 18, when valve 17 is depressed, and be applied directly onto razor blades 16 of razor 12. Once razor blades 16 are sufficiently treated, the same operations as set forth hereinabove can be performed to achieve the aforementioned advantages.

Figure 6:
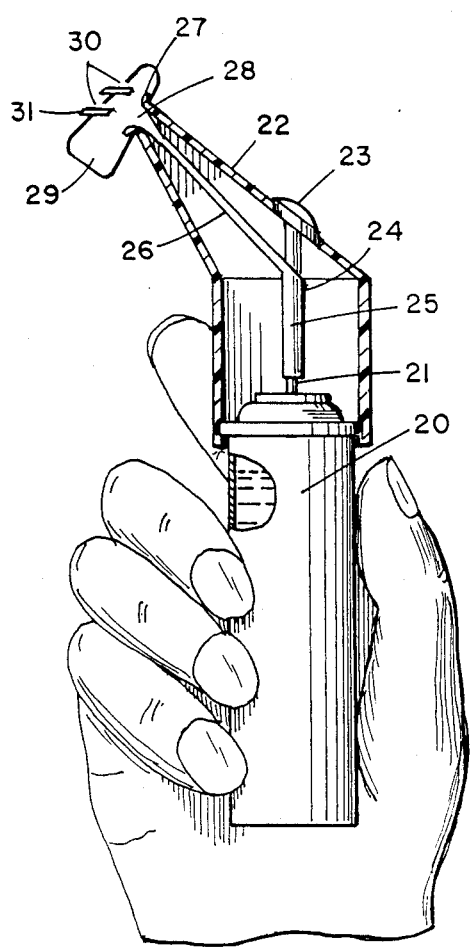
FIG. 6 is a cross-sectional view illustrating an apparatus and operation of a further alternative apparatus for use with the composition of the invention.

FIG. 6 illustrates a further alternative apparatus for use with the novel composition of the invention showing hand-held container 20 with valve means 21. Container 20 contains the novel mixture as hereinbefore described. Cap 22 is adapted to be removably secured onto container 20 and has actuator button 23 molded exteriorly thereon for axial movement through an opening sized for passage of said button. Button 23 is integrally formed with actuating stem 24 which, in turn, is in removably fixed position atop valve means 21 to communicate therewith. Stem 24 has partially hollow section 25 which is fixed to one end of flexible tube 26, the other end of which is fixed to razor head receiving element 27 to form exit port 28 thereat. Receiving element 27 is adapted to be removably engageable from razor head 29.

In operation, the user depresses actuator button 23, thereby applying a similar downward pressure via stem 24 onto valve means 21, thus allowing the mixture in container 20 to escape therefrom and through the dispensing stem defined by partially hollow section 25, flexible tube 26 and exit port 28. Upon exit from port 28, the solution creates a uniform and even dispersion through channels 30 of razor head 29 and onto razor blades 31. Once razor blades 31 are sufficiently treated, the same operations as set forth hereinabove can be performed to achieve the aforementioned advantages.

The strength of the treating effect of the present invention provides a high uniqueness of the product which reflects itself in high ratings for smooth afterfeel, closeness and smoothness of shave, razor glide, comfort of shave and overall shave quality. These findings are borne out by the data set forth in the following Table wherein forty-two (42) male panelists who wet shave daily compared the present invention against regular shaving.

Panelists washed their faces with soap and warm water, leaving the beard area wet. OLD SPICE ® shaving cream was applied by the panelist to one side of the face. Shaving proceeded with the razor rinsed under hot water each stroke. The same procedure was followed for the other half face using a new razor and the shaving composition of the present invention wherein a one second spray of the lubricant/solubilizer mixture in the aerosol system was applied after each razor rinse. After shaving, the panelist was interviewed by a technician to complete the shaving attribute responses of each shaving composition.

TABLE

| ATTRIBUTE | INVENTION | OLD SPICE ® REGULAR SHAVE CREAM |
|---|---|---|
| Shave Quality* Rating Scale Distribution: (0 = lowest, 6 = highest) | | |
| 4-6 point value | 33/79% | 29/69% |
| 0-3 point value | 9/21% | 13/31% |
| Close/Smooth Shave*** Rating Scale Distribution: (0 = lowest, 6 = highest) | | |
| 4-6 point value | 34/81% | 30/71% |
| 0-3 point value | 8/19% | 12/29% |
| Amount of Nicks/Cuts Rating Scale Distribution: (0 = lowest, 6 = highest) | | |
| 4-6 point value | 10/24% | 12/29% |
| 0-3 point value | 32/76% | 30/71% |

TABLE-continued

| ATTRIBUTE | INVENTION | OLD SPICE ® REGULAR SHAVE CREAM |
|---|---|---|
| Smooth Afterfeel* | | |
| Rating Scale Distribution: | | |
| (0 = not at all smooth, | | |
| 6 = very smooth) | | |
| 4-6 point value | 37/88% | 30/71% |
| 0-3 point value | 5/12% | 12/29% |
| Razor Glide** | | |
| Rating Scale Distribution: | | |
| (0 = lowest, 6 = highest) | | |
| 4-6 point value | 33/79% | 28/67% |
| 0-3 point value | 9/21% | 14/33% |
| Comfort of the Shave** | | |
| Rating Scale Distribution: | | |
| (0 = lowest, 6 = highest) | | |
| 4-6 point value | 33/79% | 27/64% |
| 0-3 point value | 9/21% | 15/36% |
| Compared to Regular Shave* | | |
| Rating Scale Distribution: | | |
| (−3 = worse, 0 = same, | | |
| +3 = better) | | |
| +1-+3 (better) | 28/67% | 14/33% |
| 0 (same) | 4/10% | 13/31% |
| −1-−3 (worse) | 10/23% | 15/36% |
| Convenience | | |
| (As compared to regular shave) | | |
| Rating Scale Distrbution: | | |
| (−3 = less, 0 = same, | | |
| +3 = more) | | |
| +1-+3 (more) | 25/60% | 11/26% |
| 0 (same) | 7/17% | 23/55% |
| −1-−3 (less) | 10/24% | 8/19% |
| Messiness | | |
| (As compared to regular shave) | | |
| Rating Scale Distribution: | | |
| (−3 = less, 0 = same, | | |
| +3 = more) | | |
| +1-+3 (more) | 2/5% | 8/19% |
| 0 (same) | 5/12% | 31/74% |
| −1-−3 (less) | 30/71% | 3/7% |
| Final Preference | 34/81% | 8/19% |

*Mean value at 99% Level of Confidence
**Mean value at 95% Level of Confidence
***Mean value at 90% Level of Confidence As is evident from the foregoing, the present invention achieves surprising and unexpected consumer responses with respect to shave quality, closeness and smoothness of shave, smooth after-feel, razor glide and shaving comfort. The responses are especially dramatic with respect to general comparison, convenience, messiness and final preference. This is truly surprising in view of the fact that the present invention utilizes principles which are in direct contradiction to the prior art.

Specifically, the present invention comprises a novel composition for treating the blade of a razor head by applying a non-foamable lubricant and solubilizer mixture directly thereto via an aerosolization system immediately before shaving, such that shaving can be performed in the absence of first applying any shaving preparation to the area to be shaved. Unique results are achieved.

The prior art teaches away from the present invention by utilizing principles of first wetting and moisturizing the skin with a cream, foam, gel or lotion before contacting the razor blade directly to the skin. The unique composition of the mixture achieves superior shave quality over conventional shaving systems. Accordingly, the novelty and utility of the present invention are clearly evident.

Having now described the present invention, it will be readily apparent to one skilled in the art that many variations and modifications may be made to the present invention without departing from the spirit and scope thereof.

What is claimed is:

1. A composition for treating the blade of a razor such that shaving can be performed in the absence of first applying any shaving preparation directly to the area to be shaved comprising an effective amount of a mixture a non-foaming lubricant and a solubilizer wherein said lubricant contains at least a silicone glycol copolymer.

2. The composition of claim 20 wherein said lubricant is liquid.

3. The composition of claim 2 wherein said mixture is contained in and dispersed via a pressurized container onto said razor blade.

4. The composition of claim 3 wherein said solubilizer is dimethyl ether.

5. The composition of claim 3 further comprising a fragrance.

6. The composition of claim 3 wherein said lubricant is present in an amount from about 4.0 to 20.0% by weight.

7. The composition of claim 3 wherein said solubilizer is present in an amount from about 65 to 96% by weight.

8. The composition of claim 3 wherein said fragrance is present in an amount up to about 1.0% by weight.

9. The composition of claim 3 wherein said lubricant further contains a section from the group consisting of isopropyl myristate, mineral oil, cyclomethicone, dimethicone, trimethylsiloxysilicate, 2-octyl-1-dodecanol, $C_{12}$-$C_{15}$ alcohol benzoates, myristyl propionate, sorbitan monolaurate and sorbitan monolaurate 20, and any mixtures thereof.

10. The composition of claim 3 further comprising surfactants to clean the razor blade, polymers to protect the cutting edge of said blade 1 antimicrobials to address skin ailments or mixtures thereof.

11. The composition of claim 3 wherein said solubilizer maintains a pressure of at least about 5 psig at 70° F.

12. The composition of claim 11 wherein said mixture maintains a vapor pressure of at least about 50 psig at 70° F.

13. The composition of claim 3 further comprising at least one propellant in admixture with said mixture.

14. The composition of claim 13 wherein said propellant is selected from the group consisting of propane, butane and isobutane.

15. The composition of claim 13 wherein said propellant is present in an amount up to about 14% by weight.

* * * * *